United States Patent [19]
Johnson

[11] Patent Number: 5,879,144
[45] Date of Patent: Mar. 9, 1999

[54] PRESSURE PLATE ADAPTORS AND METHODS

[75] Inventor: Jay Gregory Johnson, Maple Plain, Minn.

[73] Assignee: SIMS Deltec, Inc., St. Paul, Minn.

[21] Appl. No.: 696,533

[22] Filed: Aug. 14, 1996

[51] Int. Cl.$^6$ ................................................ F04B 43/08
[52] U.S. Cl. ........................................ 417/474; 604/153
[58] Field of Search .................................. 417/474, 417, 417/477.2; 604/153, 131, 151

[56] References Cited

U.S. PATENT DOCUMENTS

| | | |
|---|---|---|
| 3,402,673 | 9/1968 | Ballentine et al. . |
| 3,559,644 | 2/1971 | Stoft et al. . |
| 3,620,650 | 11/1971 | Shaw . |
| 4,187,057 | 2/1980 | Xanthopoulos . |
| 4,236,880 | 12/1980 | Archibald . |
| 4,482,347 | 11/1984 | Borsanyi . |
| 4,487,604 | 12/1984 | Iwatschenko et al. .................. 604/153 |
| 4,559,038 | 12/1985 | Berg et al. . |
| 4,565,542 | 1/1986 | Berg . |
| 4,585,399 | 4/1986 | Baier . |
| 4,650,469 | 3/1987 | Berg et al. . |
| 4,657,486 | 4/1987 | Stempfle et al. . |
| 4,671,792 | 6/1987 | Borsanyi . |
| 5,017,059 | 5/1991 | Davis . |
| 5,074,756 | 12/1991 | Davis . |
| 5,078,683 | 1/1992 | Sancoff et al. . |
| 5,165,874 | 11/1992 | Sancoff et al. . |
| 5,211,548 | 5/1993 | Okada ................................. 604/153 X |
| 5,213,483 | 5/1993 | Flaherty et al. . |
| 5,226,886 | 7/1993 | Skakoon et al. . |
| 5,336,190 | 8/1994 | Moss et al. . |
| 5,397,222 | 3/1995 | Moss et al. . |
| 5,425,173 | 6/1995 | Moss et al. . |
| 5,531,697 | 7/1996 | Olsen et al. . |
| 5,564,915 | 10/1996 | Johnson . |
| 5,626,563 | 5/1997 | Dodge et al. ........................... 604/153 |

FOREIGN PATENT DOCUMENTS

| | | |
|---|---|---|
| WO 93/10853 | 6/1993 | WIPO . |
| WO 96/27402 | 9/1996 | WIPO . |
| WO 97/02059 | 1/1997 | WIPO . |

OTHER PUBLICATIONS

Photographs of a pump product by Patient Solutions, Inc., Med–mate ™, Model 1100, pp. A1–A5.

Photographs of a pump product by Block Medical, Inc., a Hillenbrand Industry, Verifuse® Model No. B001500, pp. B1–B3.

Photographs of a pump product by Medfusion, Inc., a Medex, Inc. Company, Infu–Med™, WalkMed™ 440 PIC, pp. C1–C2.

Photographs of a pump product by C.R. Bard, Inc., Bard Medsystems Division, pp. D1–D3.

Photographs of a pump product by Pharmacia Deltec, Inc., pp. E1–E2.

(List continued on next page.)

*Primary Examiner*—Ismael Izaguirre
*Attorney, Agent, or Firm*—Merchant, Gould, Smith, Edell, Welter & Schmidt, P.A.

[57] ABSTRACT

A pressure plate for use with a pump includes a top surface configured for receipt of a tube and a plurality of side edges defining a channel communicating with the top surface. The pressure plate also includes a pair of hooks and a loop for releasably attaching the pressure plate to the pump. Attachment structure is provided for fixedly attaching the first end of the top surface to the pump. A method for attaching to a pump a reservoir having a tube includes providing a pressure plate with first and second ends and having an inlet tube slot and an outlet tube slot for holding the tube; attaching the first end of the pressure plate to the pump using a fastener, the fastener allowing the pressure plate to pivot toward and away from the pump; inserting the tube into the inlet tube slot and outlet tube slot; pivoting the second end of the pressure plate toward the pump; and attaching the second end of the pressure plate to the pump.

31 Claims, 3 Drawing Sheets

OTHER PUBLICATIONS

Photographs of a pump product by AVI, Inc., AVI Guardian™ Micro 110, pp. F1–F4.

Photographs of a pump product by Abbott Laboratories, Abbott/Shaw LifeCare®Pump Model 3, pp. G1–G3.

Patient Solutions, Inc. literature for MedMate™ 1100, 2 pages.

Patient Solutions, Inc. Directions for Use, MedMate™ model 1100, 61 pages.

Block Medical, Inc. literature for Verifuse System, 1 page, dated Nov. 1990.

Medifusion, Inc. Operations Manual for Medifusion WALKMED™Ambulatory Infusion Pump, 92 pages, dated Apr. 1990.

Medex Ambulatory Infusion Systems literature,entitled "WalkMed Pump Disposable Products," 2 pages, dated 1992.

Medex Ambulatory Infusion Systems literature, entitled "WalkMed PCA," 2 pages, dated 1993.

Bard Ambulatory PCA Pump literature, 2 pages, dated Jun. 1990.

Bard MedSystems Division, C.R. Bard, Inc. Quick Reference Guide, 2 pages, dated Feb. 1992.

Bard MedSystems Division, C.R. Bard, Inc., Bard® Ambulatory PCA Pump Operator's Manual, 43 pages, dated Apr. 1990.

AVI, Inc. literature entitled "The AVI Advantage,", 2 pages, dated 1983.

AVI, Inc. literature, entitled "Bridging the Gap," 6 pages, datd Apr. 22, 1983.

Abbott Laboratories Hospital Products Division literature, entitled "The Blue Line System LifeCare®," 16 pages, dated Jul. 1990.

Abbott Laboratories Hospital Products Division literature, entitled "LifeCare® Electronic Flow Control Systems Catalog," 34 pages, dated May, 1985.

PRESSURE PLATE ADAPTORS AND METHODS

FIELD OF THE INVENTION

This invention relates generally to medical devices. More particularly, this invention relates to a pressure plate for use with a pump and methods of use.

BACKGROUND OF THE INVENTION

In medical applications, it is sometimes necessary to deliver fluid intravenously to a patient undergoing treatment. The fluid may be contained in a bag or other fluid reservoir, conveyed through a tube, and inserted into the patient's vein. At times, the amount of fluid conveyed to the patient must be controlled or regulated. In those instances where the fluid to the patient must be controlled, pumps have been used.

One pump is described in U.S. Pat. No. 4,559,038. This pump controls the delivery of fluid from the reservoir to the patient. In the '038 patent, the fluid is in a bag held in a container, or cassette, immediately adjacent to the pump. The pump controls the amount of fluid to the patient by physically pressuring the tube from the bag to the patient, and restricting the volume of fluid allowed to flow to the patient. The pump includes a pump mechanism which engages the tube and squeezes the tube against a pressure plate of the cassette to effect pumping of fluid.

It is also known to use the pump with a fluid reservoir that is remote, or separate from the pump. Typically, in a remote system, the fluid is contained in a bag and hung on a device separate from the pump. The bag has a tube extending from the bag, across a section of the pump, and then to the patient. Again, the pump controls the amount of fluid to the patient by mechanical pressure on the tube. A pressure plate mounted to the pump allows the pump mechanism to engage the tube to effect pumping.

In the past, certain types of pressure plates have been used to connect the pump to the tube. Because of reasons such as safety and cleanliness, the pressure plate is permanently attached to the tube. When the fluid reservoir is empty, or the treatment to the patient completed, the reservoir, tube, and pressure plate are all thrown away. Disposing of the pressure plate contributes to waste and expense. There is a need for systems and methods that allow reuse of the pressure plate. For reusable pressure plates, there is also a need for systems and methods that allow for selective detachment of the pressure plate from the pump, even during periods of nonuse.

SUMMARY OF THE INVENTION

The invention comprises a pressure plate for use with a pump. The pressure plate includes a top surface having first and second ends and is configured for receipt of a tube. A plurality of side edges are substantially orthogonal to the top surface, and the side edges define a channel communicating with the top surface. A pair of hooks and a loop are on the top surface for releasably attaching the pressure plate to the pump. Attachment structure is provided for fixedly attaching the first end of the top surface to the pump.

Preferably, the pair of hooks are at the first end and are for engaging mating structure on the pump. Further, the loop is at the second end for engaging mating structure on the pump.

Preferably, the attachment structure includes a fastener connecting the pressure plate to the pump. The fastener may be a set screw, or a pair of set screws.

The channel includes at least one of the side edges defining a first tube slot for accommodating a first end of the tube. Preferably, a second of the side edges defines a second tube slot for accommodating a second end of the tube. The first and second tube slots may have dimensions smaller than a dimension of the tube to create an interference fit between the slots and the tube.

The top surface may include a plurality of ribs between the first tube slot and the second tube slot for engaging and centering the tube.

In another aspect, the invention comprises a method for attaching to a pump a reservoir having a tube. The method includes providing a pressure plate having first and second ends, and having an inlet tube slot and an outlet tube slot for holding the tube; attaching the first end of the pressure plate to the pump using a fastener, the fastener allowing the pressure plate to pivot toward and away from the pump; inserting the tube into the inlet tube slot and outlet tube slot; pivoting the second end of the pressure plate toward the pump; and attaching the second end of the pressure plate to the pump.

In certain implementations, the step of inserting the tube may be performed prior to the step of attaching the first end. In other implementations, the step of inserting the tube is performed after the step of attaching the first end.

Preferably, the step of attaching the first end of the pressure plate to the pump using a fastener includes inserting a set screw to connect the pressure plate to the pump.

In another aspect, the invention comprises a system including a pump and a pressure plate. The pressure plate includes a pair of hooks and a loop for releasably attaching the pressure plate to the pump, and attachment structure constructed and arranged for fixedly attaching the pressure plate to the pump.

Preferably, the system further includes a fluid reservoir having a tube, and the pressure plate is configured for holding the tube.

In certain applications, the pressure plate includes a top surface having first and second ends, and a plurality of side edges substantially orthogonal to the top surface. The side edges define a channel communicating with the top surface.

Preferably, the pair of hooks are at the first end of the pressure plate, and the loop is at the second end of the pressure plate. The attachment structure may include a fastener at the first end of the pressure plate.

Preferably, a tube is held in the pressure plate by the channel. The tube may be attached to a fluid reservoir.

DETAILED DESCRIPTION OF THE PREFERRED EMBODIMENTS

Figure 2:
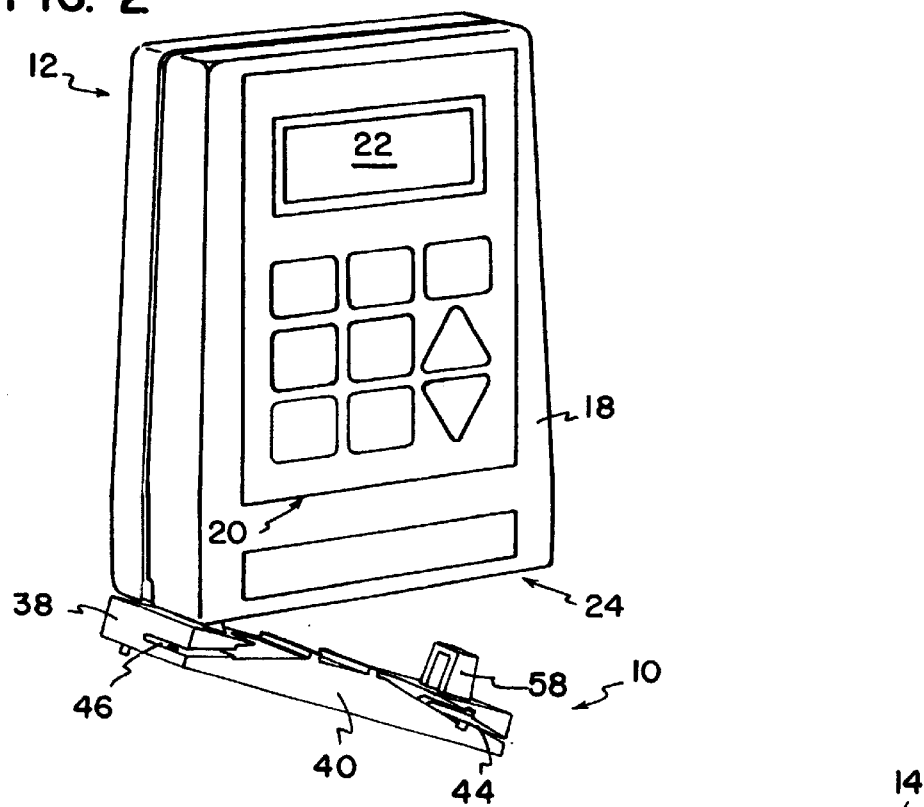
FIG. 2 is a perspective view of the pump and the pressure plate of the system shown in FIG. 1 and according to the present invention.

The invention relates to a pressure plate for use with a pump. The pressure plate and pump may be part of a system for conveying fluid from a fluid reservoir, to a tube, and finally to the patient, such as the patient's vein. The pressure plate is reusable with the pump to pump fluid through different tubes, which can be disposed of after use. The pressure plate includes a mounting arrangement with the pump such that the pressure plate remains mounted to the pump, but the tube can be removed and replaced with a second tube. The mounting arrangement allows a pressure plate with two hooks and a loop to be pivotally mounted to the pump so as to remain with the pump during replacement of the tube. The mounting arrangement adapts a pressure plate design that was otherwise completely separable from the pump to be mounted to the pump during tube replacement.

Reference will now be made in detail to the present preferred embodiment of the invention wherein like reference numerals indicate like elements through the several views. As embodied herein, a pressure plate is shown generally at 10 for use with a pump shown at 12. Pump 12 controls the amount of fluid conveyed from a fluid reservoir 14 through a tube 16 to the patient.

Figure 5:
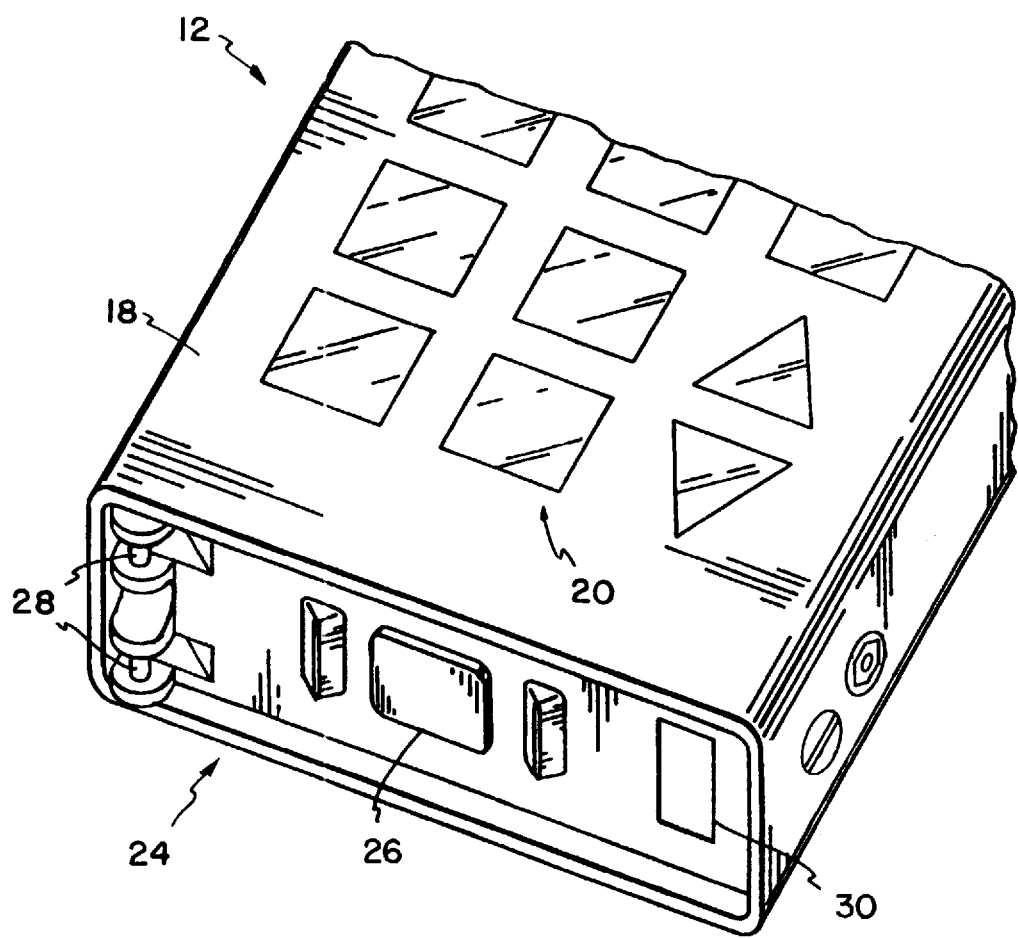
FIG. 5 is a further perspective view of the pump.

Pump 12 includes a control and display face 18. Control and display face 18 includes various control keys or buttons 20 for operating pump 12, and includes a display 22 for providing input and output information to the pump operator. Orthogonal to control and display face 18 is a tube interface region 24, shown best in FIG. 5. Tube interface region 24 includes tube engaging members 26 for applying pressure to tube 16 in order to control the volume of fluid conveyed from fluid reservoir 14 to the patient.

The pump also includes structure for mating with the pressure plate. In the particular embodiment shown in FIG. 5, tube interface region 24 of pump 12 includes a pair of pins 28 which are permanently attached at one end of pump 12. At an opposite end of pump 12, a cavity 30 is defined in tube interface region 24. As will be explained in more detail below, pins 28 and cavity 30 cooperate with mating structure on pressure plate 10 in order to hold tube 16 in engagement with tube engaging members 26.

Figure 3:
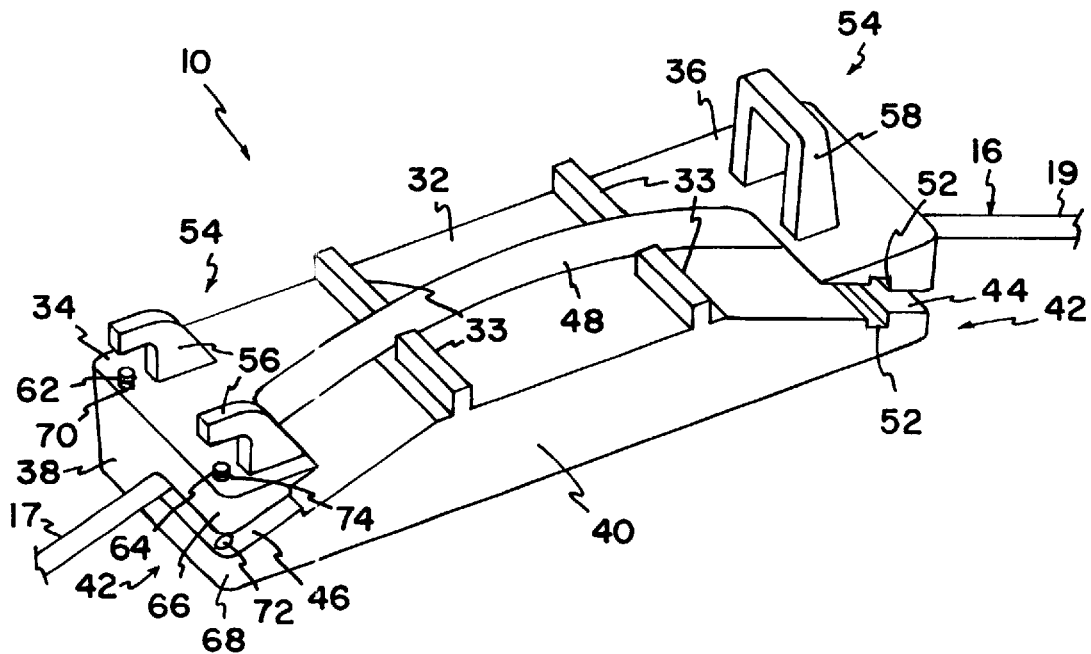
FIG. 3 is a perspective view of the pressure plate of the system of FIG. 1 and according to the present invention.

In accordance with the invention, the pressure plate includes a top surface having first and second ends, and is configured for receipt of a tube. In the particular embodiment illustrated in FIG. 3, pressure plate 10 is shown as having a top surface 32 and includes a first end 34 and a second end 36. As illustrated in FIG. 3, tube 16 extends across the entire top surface 32 of pressure plate 10 from first end 34 to second end 36. Top surface 32 includes a plurality of ribs 33. Ribs 33 extend laterally from second side edge 40 to the opposite edge, as illustrated in FIG. 3. Ribs 33 define notches or gaps for allowing a large diameter portion 48 of tube 16 to pass through. Tube 16 also includes a first small diameter portion 17 and a second small diameter portion 19. Ribs 33 engage and hold the tube securely in place on pressure plate 10 to allow tube engaging members 26 of pump 12 to act on it.

Pressure plate 10 may be a variety of shapes and sizes. In the particular embodiment illustrated, pressure plate 10 is generally rectangularly sized to mate with tube interface region 24 of pump 12. Specifically, in the particular embodiment illustrated, a plurality of side edges are substantially orthogonal to top surface 32. A first side edge 38 is illustrated as adjacent to first end 34 and orthogonal to top surface 32. A second side edge 40 is orthogonal to top surface 32 and runs the length of pressure plate 10, spanning from first end 34 to second end 36. Third and fourth side edges are opposite to first and second side edges, respectively. Although the illustrated embodiment shows side edges as being generally orthogonal, it should be understood that a precise 90 degree angle is not required. For example, the side edges could be an acute angle with respect to the top surface. An orthogonal angle was chosen in the illustrated embodiment for the ease of manufacturing.

In accordance with the invention, the side edges define a channel communicating with the top surface. As embodied herein, a channel is shown generally at 42. Channel 42 is generally a cavity extending from the side edges to top surface 32, and which functions to allow tube 16 to be inserted into pressure plate 10, without having to entirely remove pressure plate 10 from its connection to pump 12.

Figure 4:
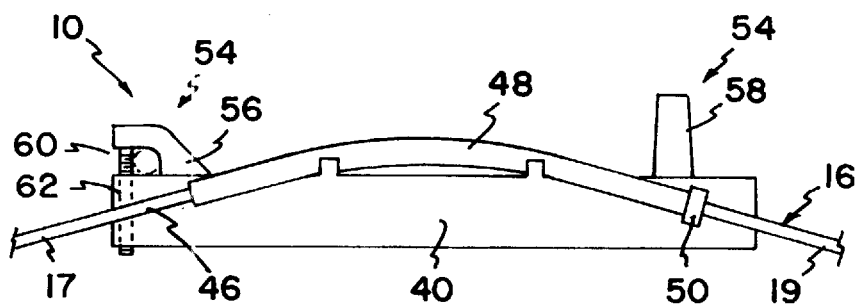
FIG. 4 is an elevational view of the pressure plate of FIG. 3 and according to the present invention.

A keying system is provided for allowing a tube to be easily inserted and replaced in a pressure plate, while also ensuring the proper use and precluding the improper removal of the tube from the pressure plate. As embodied herein, a keying system includes the cooperation of certain features on tube 16 with certain features of channel 42. Specifically, tube 16 includes the large diameter portion 48, as illustrated in FIGS. 3 and 4. Further, tube 16 includes a rigid plastic ring 50 (FIG. 4) which completely surrounds the circumference of tube 16. Rigid plastic ring 50 is securely mounted to tube 16, and is not allowed to slide along the surface of tube 16. The function of large diameter portion 48 and ring 50 will be explained below in conjunction with the details regarding channel 42.

Channel 42 includes an inlet tube slot 44 and an outlet tube slot 46. Inlet tube slot 44 is generally an elongated cavity extending from second side edge 40 through pressure plate 10 and communicating with top surface 32. Inlet tube slot 44 includes a T-slot 52 for accommodating ring 50 of tube 16. In other words, in order to insert tube 16 into pressure plate 10, ring 50 must be aligned with T-slot 52 in order to slide tube 16 into inlet tube slot 44.

Outlet tube slot 46 is a generally elongated cavity extending from second side edge 40 to first side edge 38 and communicating with top surface 32. Outlet tube slot 46 is a voided area between an upper portion 66 and lower portion 68 of pressure plate 10. Outlet tube slot 46 allows first small diameter portion 17 of tube 16 to be slideably accommodated and held within outlet tube slot 46, that is, between upper portion 66 and lower portion 68. Outlet tube slot 46 is sized to have a width which is somewhat smaller than the diameter of large diameter portion 48 of tube 16. This function is to prevent the inadvertent or improper removal of tube 16 from pressure plate 10 by longitudinal pull, or otherwise. Outlet tube slot 46 is sized smaller than the outer diameter of ring 50. Because of this, tube 16 may only be installed in pressure plate 10 in one way, i.e., with ring 50 passing through T-slot 52. This will prevent the medical professional from installing tube 16 backwards. The T-slot may be placed on the outlet tube slot, instead of the inlet tube slot. Other ways of implementing the keying system of the invention are contemplated so as to prevent the tube from being installed backwards, and to prevent the tube from being displaced longitudinally relative to the pressure plate.

Figure 1:
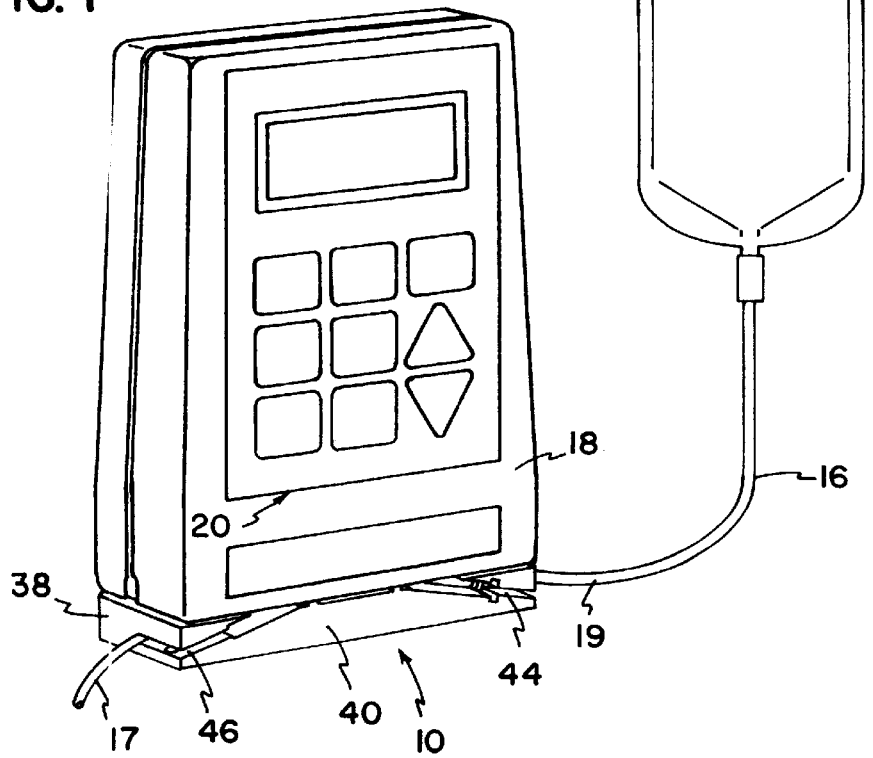
FIG. 1 is a perspective view of an embodiment of a system according to the present invention.

In accordance with the invention, a pressure plate includes first attachment structure on the top surface constructed and arranged for releasably attaching the pressure plate to the pump. In the particular embodiment shown in the Figures, first attachment structure is shown generally at 54. Specifically, in one embodiment shown in FIGS. 3 and 4, first attachment structure includes a pair of hooks 56 at first end 34 for engaging mating structure on pump 12. Hooks 56 are generally L shaped structures which engage pins 28, shown in FIG. 5 of pump 12. Hooks 56 engaging with pins 28 allow pressure plate 10 to pivot toward and away from pump 12. This pivoting action is illustrated in FIGS. 1 and 2. In FIG. 1, pressure plate 10 is pivoted toward pump 12 and is intimately adjacent to pump 12 to allow the pump to act on tube 16. In FIG. 2, pressure plate 10 is pivoted away from pump 12. The FIG. 2 position is achieved when a new tube 16 is being inserted into pressure plate 10.

First attachment structure 54 also includes a loop 58 at second end 36 of pressure plate 10. Loop 58 engages and is completely inserted within cavity 30 of pump 12. Pump 12 includes conventional mechanical structure (a latch) which engages the inner part of loop 58 to lock loop 58 to pump 12. In FIG. 1, loop 58 is encased in cavity 30 and is locked to pump 12. Loop 58 can be slotted if desired. In such a case, tube 16 need not be positioned in any tube slot 44, and instead can be positioned along top surface 32, and possibly held in place with a clip.

In accordance with the invention, a pressure plate includes second attachment structure for fixedly attaching the first end of the top surface to the pump. As embodied herein and illustrated in FIG. 4, second attachment structure is shown generally at 60. Second attachment structure may be any of a variety of mechanisms which will fixedly and securely connect one end of pressure plate 10 to pump 12. In the particular arrangement shown in FIGS. 3 and 4, second attachment structure 60 includes a first and second set screw 62, 64. First set screw 62 passes through a threaded hole 70 in pressure plate 10 and mates with a threaded hole in pump 12. Second set screw 64 is a much shorter length than first set screw 62 because it only passes through upper portion 66 of pressure plate 10, although lower portion 68 includes a hole 72 in order to allow a tool to pass through to engage second set screw 64 and tighten second set screw 64 in its mating threaded 74 hole in pump 12.

Through a combination of hooks 56 and second attachments structure 60, pressure plate 10 is allowed to be securely attached to pump 12, but still allows for the convenient and easy insertion and removal of tube 16. In prior systems, in order to provide a new tube, the entire pressure plate would have to be removed from the pump and thrown away. Under the new system, the pressure plate is reusable and is still secure and safe to use. Also, the new system prevents the pressure plate from being misplaced during nonuse of the pump. The pressure plate may be disconnected altogether from the pump, by releasing the fasteners and removing the pressure plate. This way, the pump may still be used with disposable pressure plates.

The second attachment structure 60 may include other arrangements. For example, the second set screw 64 may be omitted altogether, with just first set screw 62 functioning to secure pressure plate 10 to pump 12. Further, other types of fasteners may be used as alternatives to set screws.

Because the pressure plate is reusable, suitable materials for its construction are desired so as to ensure proper mounting to the pump and proper fluid delivery. The material or materials selected should withstand repeated reuses with the pump a suitable number of times and also allow the pump to pump properly without free flow or without requiring excessive energy drain and/or causing a stoppage of the pumping mechanism. All metal, molded plastic with metal reinforcement, and glass-filled plastic are possible constructions for a reusable pressure plate.

In operation, the pressure plate attaches the pump to a reservoir having a tube as follows: First end 34 of pressure plate 10 is attached to pump 12. This is accomplished by first engaging hooks 56 with pins 28. Next, second attachment structure 60 is used in order to permanently and fixedly secure pressure plate 10 to pump 12. Specifically, in the embodiment illustrated, first and second set screws, 62, 64 are rotated and tightened into their mating threaded holes in pump 12. This secures pressure plate 10 into the position shown in FIG. 2. Next, tube 16 is inserted into pressure plate 10 by finding ring 50 and aligning it with T-slot 52 into inlet tube slot 44. Large diameter portion 48 of tube 16 is placed in the notches of ribs 33, and the rest of tube 16 is slid into outlet tube slot 46 between upper and lower portions 66, 68. This step of inserting the tube into the inlet tube slot and outlet tube slot may be performed prior to the step of attaching the first end of the pressure plate to the pump. Next, second end 36 of pressure plate 10 is pivoted toward pump 12 to the position shown in FIG. 1. Loop 58 is completely inserted within cavity 30, and a latch in the pump engages loop 58 to lock pressure plate into the position shown in FIG. 1. To remove the pressure plate from the pump, the above steps are executed in reverse.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pressure plate for use with a pump, the pressure plate comprising:

a top surface having first and second ends and being configured for receipt of a tube;

a plurality of side edges substantially orthogonal to the top surface, the side edges defining a channel communicating with the top surface;

a pair of hooks and a loop on the top surface for releasably attaching the pressure plate to the pump; and attachment structure constructed and arranged for fixedly attaching the first end of the top surface to the pump, the second end being selectively moveable relative to the pump when the first end is fixedly attached to the pump.

2. The pressure plate of claim 1, wherein the pair of hooks are at the first end for engaging mating structure on the pump.

3. The pressure plate of claim 2, wherein the loop is at the second end for engaging mating structure on the pump.

4. The pressure plate of claim 1, wherein the attachment structure includes a fastener connecting the pressure plate to the pump.

5. The pressure plate of claim 4, wherein the fastener is a set screw.

6. The pressure plate of claim 1, wherein the attachment structure includes a pair of set screws connecting the pressure plate to the pump.

7. The pressure plate of claim 1, wherein the channel includes:

one of the side edges defining an inlet tube slot for accommodating a first end of the tube; and a second of the side edges defining an outlet tube slot for accommodating a second end of the tube.

8. The pressure plate of claim 7, further comprising a keying system to ensure that the tube is properly installed in the pressure plate.

9. The pressure plate of claim 8, wherein the keying system includes a T-slot in the inlet tube slot adapted for accommodating a ring on the tube.

10. The pressure plate of claim 7, wherein the attachment structure includes a set screw.

11. A method for mounting a pressure plate and a tube to a pump, the method comprising the steps of:
providing the pressure plate and the tube, the pressure plate having first and second ends, two hooks at the first end, and a loop at the second end, and having an inlet tube slot and an outlet tube slot for holding the tube;
pivotally mounting the first end of the pressure plate to the pump using a fastener, the pivotal mounting allowing the pressure plate to pivot toward and away from the pump, the step of pivotally mounting including the step of surrounding a portion of the pump with the fastener and one of the hooks;
inserting the tube into the inlet tube slot and outlet tube slot;
pivoting the second end of the pressure plate toward the pump; and
mounting the second end of the pressure plate to the pump.

12. The method of claim 11, wherein the step of inserting the tube is performed prior to the step of pivoting mounting the first end.

13. The method of claim 11, wherein the step of inserting the tube is performed after the step of pivoting mounting the first end.

14. The method of claim 11, wherein the step of pivoting mounting the first end of the pressure plate to the pump using a fastener includes inserting a set screw to connect the pressure plate to the pump.

15. The method of claim 11, further comprising the step of disconnecting the pressure plate from the pump.

16. The pressure plate of claim 1, wherein the first end is further pivotally attached to the pump at the hooks.

17. A medical infusion pump system comprising:
a pump; and
a pressure plate including:
a pair of hooks and a loop for releasably attaching the pressure plate to the pump;
attachment structure constructed and arranged for fixedly attaching the pressure plate to the pump;
a first end for fixedly attaching to the pump with the attachment structure; and
a second end which is selectively moveable when the first end is fixedly attached to the pump.

18. The system of claim 17, further comprising a fluid reservoir having a tube, the pressure plate being configured for holding the tube.

19. The system of claim 17, wherein the pressure plate includes:
a top surface having first and second ends; and
a plurality of side edges substantially orthogonal to the top surface, the side edges defining a channel communicating with the top surface.

20. The system of claim 19, wherein the pair of hooks are at the first end of the pressure plate and mateably engage a pair of pins on the pump.

21. The system of claim 19, wherein the attachment structure includes a fastener at the first end of the pressure plate.

22. The system of claim 19, further comprising a tube being held in the pressure plate by the channel.

23. The system of claim 22, wherein the tube is attached to a fluid reservoir.

24. The system of claim 22, further comprising a keying system to ensure that the tube is properly installed in the pressure plate.

25. The system of claim 24, wherein the keying system includes a ring on the tube, a T-slot in the channel, and a large diameter portion on the tube.

26. The system of claim 24, further comprising a plurality of ribs engaging preceding the single occurrence of "large diameter portion", a large diameter portion of the tube.

27. The system of claim 21, further comprising a pair of pins on the pump for engaging the pair of hooks.

28. The system of claim 27, wherein the fastener engages at least one of the hooks to trap at least one of the pins between the at least one hook and the fastener.

29. The system of claim 17, wherein the first end is further pivotally attached to the pump at the hooks.

30. A method for mounting a pressure plate and a tube to a pump, the method comprising the steps of:
providing the pressure plate and the tube, the pressure plate having an inlet tube slot and an outlet tube slot for holding the tube;
pivotally mounting the first end of the pressure plate to the pump using a fastener, the pivotal mounting allowing the pressure plate to pivot toward and away from the pump, the fastener selectively moveable relative to the pressure plate, the step of pivotally mounting including the step of moving the fastener so as to surround a portion of the pump with the fastener and a portion of the pressure plate;
inserting the tube into the inlet tube slot and outlet tube slot after mounting the first end of the pressure plate to the pump using the fastener;
pivoting the second end of the pressure plate toward the pump; and
mounting the second end of the pressure plate to the pump.

31. A method for mounting a pressure plate and a tube to a pump, the method comprising the steps of:
providing the pressure plate and the tube, the pressure plate having an inlet tube slot and an outlet tube slot for holding the tube;
pivotally mounting the first end of the pressure plate to the pump using a set screw to connect the pressure plate to the pump, the pivotal mounting allowing the pressure plate to pivot toward and away from the pump, the set screw selectively moveable relative to the pressure plate, the step of pivotally mounting including the step of moving the set screw so as to surround a portion of the pump with the set screw and a portion of the pressure plate;
inserting the tube into the inlet tube slot and outlet tube slot;
pivoting the second end of the pressure plate toward the pump; and
mounting the second end of the pressure plate to the pump.

* * * * *

UNITED STATES PATENT AND TRADEMARK OFFICE
CERTIFICATE OF CORRECTION

PATENT NO. : 5,879,144

DATED : March 9, 1999

INVENTOR(S) : JOHNSON

It is certified that error appears in the above-identified patent and that said Letters Patent is hereby corrected as shown below:

In Claim 26, Column 8, lines 11–12, delete "preceding the single occurrence of 'large diameter portion',"

Signed and Sealed this

Twentieth Day of June, 2000

Attest:

Q. TODD DICKINSON

*Attesting Officer*  *Director of Patents and Trademarks*